US008244361B1

(12) United States Patent  
De Ridder

(10) Patent No.: US 8,244,361 B1
(45) Date of Patent: Aug. 14, 2012

(54) STIMULATION SYSTEM AND METHOD FOR TREATING FRAGILE BONE DISORDERS

(75) Inventor: Dirk De Ridder, Zelzate (BE)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1146 days.

(21) Appl. No.: 12/109,819

(22) Filed: Apr. 25, 2008

Related U.S. Application Data

(60) Provisional application No. 60/914,200, filed on Apr. 26, 2007, provisional application No. 60/938,600, filed on May 17, 2007.

(51) Int. Cl.
*A61N 1/00* (2006.01)

(52) U.S. Cl. .......................................... 607/51

(58) Field of Classification Search ............... 607/51, 607/117
See application file for complete search history.

(56) References Cited

U.S. PATENT DOCUMENTS

| 7,149,574 B2 | 12/2006 | Yun et al. | |
|---|---|---|---|
| 2006/0047325 A1* | 3/2006 | Thimineur et al. | 607/45 |
| 2006/0111754 A1 | 5/2006 | Rezai et al. | |

OTHER PUBLICATIONS

Yirmiya, et al., "Depression induces bone loss through stimulation of the sympathetic nervous system," Proc. Natl. Acad. Sci., USA, Nov. 7, 2006, vol. 103, No. 45, pp. 16876-16881.
Kondo, et al., "Unloading Induces Osteoblastic Cell Suppression and Osteoclastic Cell Activation to Lead to Bone Loss via Sympathetic Nervous System," The Journal of Biological Chemistry, USA, Aug. 26, 2005, vol. 280, No. 34, pp. 30192-30200.

* cited by examiner

*Primary Examiner* — Mark W Bockelman
(74) *Attorney, Agent, or Firm* — Christopher S. L. Crawford; Craig Hoersten; Peter R. Lando

(57) ABSTRACT

According to one aspect, a stimulation system is provided for electrically stimulating a predetermined site to treat a fragile bone disorder or condition. The system includes an electrical stimulation lead adapted for implantation into a subcutaneous area in communication with a predetermined site, wherein the site is neuronal tissue that is associated with C2/C3 dermatome area. The stimulation lead includes one or more stimulation electrodes adapted to be positioned in the predetermined site. The system also includes a stimulation source that generates the stimulation pulses for transmission to the one or more stimulation electrodes of the stimulation lead to deliver the stimulation pulses to the predetermined site to treat a fragile bone disorder or condition.

9 Claims, 4 Drawing Sheets

STIMULATION SYSTEM AND METHOD FOR TREATING FRAGILE BONE DISORDERS

CROSS-REFERENCE TO RELATED APPLICATIONS

This application claims the benefit of U.S. Provisional Application No. 60/914,200, filed Apr. 26, 2007 and U.S. Provisional Application No. 60/938,600, filed May 17, 2007, the disclosures of which are fully incorporated herein by reference.

BACKGROUND

This application relates to neuronal tissue stimulation for treating fragile bone disorders, such as osteoporosis, and more particularly to modulating neuronal tissue in the C2/C3 dermatome area, or stimulating cervical nerve roots and/or stimulating cranial nerves.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue. Estrogen is an example of an anti-resorptive agent. It is known that estrogen reduces fractures. In addition, Black, et al. in EP 0605193A1 report that estrogen, particularly when taken orally, lowers plasma levels of low density lipoproteins (LDL's) and raises those of the beneficial high density lipoproteins (HDL's). However, estrogen failed to restore bone back to young adult levels in the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporotic skeleton. Such agents can include prostaglandin agonists as described in U.S. Pat. No. 4,112,236, GB 1478281, GB1479156, U.S. Pat. Nos. 4,175,203, 4,055,596, 4,175,203, 3,987,091 and 3,991,106.

Recently, a link between the sympathetic nervous system and the skeletal system has been established. For example, increases in sympathetic tone mediates bone loss through suppression of bone formation by enhancement of osteoclast activity and reduction in osteoblast activity (Kondo et al., J Biol Chem. 2005 Aug. 26; 280(34):30192-200). Yirmirya et al., have recently shown that major depression results in an increase in bone norepinephrine levels resulting in increases in bone loss (Yirmiya et al., Proc Natl Acad Sci USA. 2006 Nov. 7; 103:16876-81).

Although there are a variety of osteoporosis therapies there is a continuing need and a continuing search in this field of art for alternative osteoporosis therapies. In addition, there is a need for bone fracture healing therapies. The present inventor is the first to utilize neurostimulation of the peripheral nervous system to treat bone loss or fragile bone disorders/diseases, such as osteoporosis.

SUMMARY

The present application is designed for the treatment of any type of fragile bone condition or any disorder relating to bone loss including but not limited to osteoporosis, age-associated osteoporosis, postmenopausal osteoporosis, osteitis deformans (Paget's disease), osteogenesis imperfecta (brittle bones), and osteopetrosis, osteoarthrosis/osteoarthritis. The degeneration of joints or osteoarthrosis as it is called in Europe or osteoarthritis as it is called in the USA, are also included.

According to one aspect, a neurological stimulation system is provided for electrically stimulating a predetermined site, for example a cervical dermatome area (e.g., C2 dermatome area/C3 dermatome area), cervical nerve roots and/or cranial nerves to treat one or more fragile bone disorders, such as osteoporosis. The system includes an electrical stimulation lead adapted for implantation into a subcutaneous area in communication with the predetermined site for electrical stimulation of the predetermined site, more particularly the C2/C3 dermatome area. The stimulation lead includes one or more stimulation electrodes adapted to be positioned in the subcutaneous area of the predetermined site to deliver electrical stimulation pulses to the predetermined site. The system also includes a stimulation source that generates the electrical stimulation pulses for transmission to the one or more stimulation electrodes of the stimulation lead. The stimulation of the site, for example the C2/C3 dermatome, can result in decreases in norepinephrine and other catecholamine concentrations, increases in osteoblast activity, and/or decreases in osteoclast activity thereby reducing, abrogating or treating fragile bone disorders. Yet further, the system includes a means for programming the stimulation source, for example a hand-held programmer can be used to externally program the stimulation source.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

For a more complete understanding of the present application, reference is now made to the following descriptions taken in conjunction with the accompanying drawing, in which.

DETAILED DESCRIPTION

I. Definitions

Figure 1:
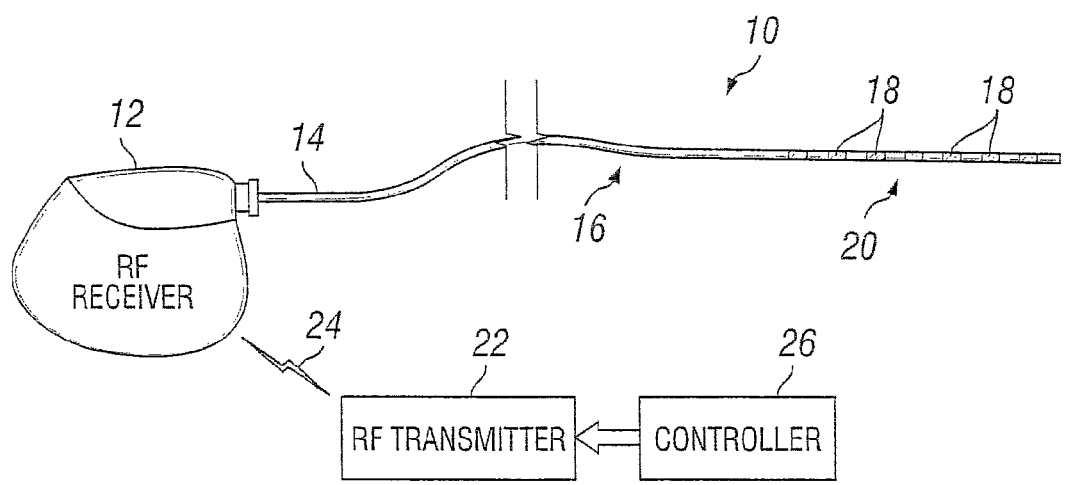
FIG. 1 illustrates an example neurological stimulation system for electrically stimulating peripheral nerves or neuronal tissue to treat one or more fragile bone disorders or conditions.
Figure 2A:
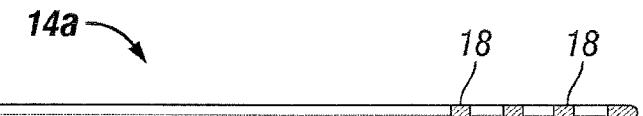
FIGS. 2A-2I illustrate example electrical stimulation leads that may be used to electrically stimulate the peripheral nerves or neuronal tissue to treat one or more fragile disorders or conditions.
Figure 2B:
Figure 2C:
Figure 2D:
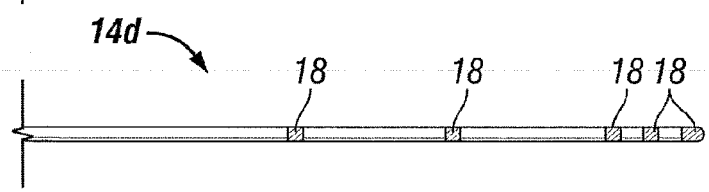
Figure 2E:
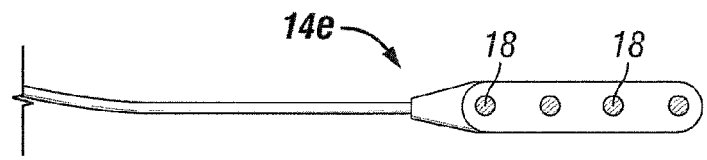
Figure 2F:
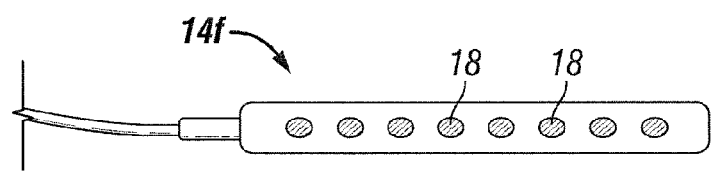
Figure 2G:
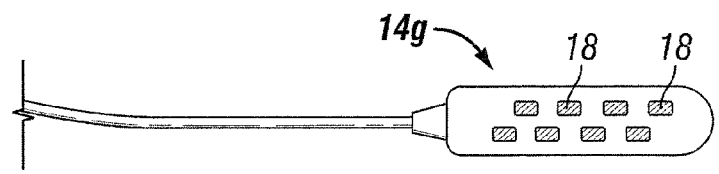
Figure 2H:
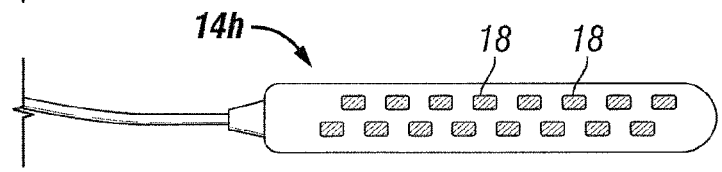
Figure 2I:
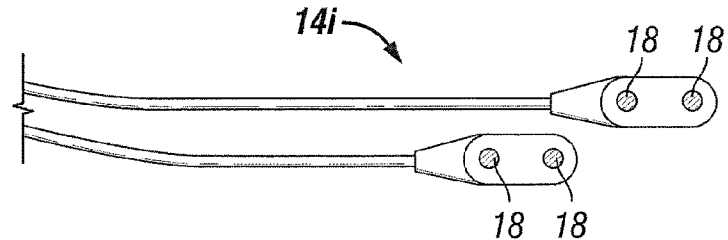

Unless defined otherwise, technical and scientific terms used herein have the same meaning as commonly understood by one of ordinary skill in the art. For purposes of the present application, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "bone remodeling" as used herein refers to the process of renewing the skeleton and maintaining the strength of bone. This process occurs throughout the lifetime of the subject. Two reactions are involved in the process of bone remodeling, bone loss or resorption and bone growth or accretion. This remodeling occurs in a series of discrete pockets of activity in the bone. These pockets are lined with two different cell types called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

The term "fragile bone condition" or "fragile bone disease" as used herein refers to a condition or disease characterized by low bone mass or structural deterioration of bone tissue, leading to bone fragility and increased susceptibility to fractures.

The term "type I osteoporosis" or "postmenopausal osteoporosis" as used herein is usually found in women after the beginning of menopause. The incidence in women is six to eight times higher than that in men. It has been postulated that the cause of this osteoporosis is accelerated bone resorption. The increased bone turnover results in a secondary decrease in parathyroid hormone (PTH) secretion as well as a secondary reduction in the renal production of calcitriol. Patients present with trabecular bone loss with vertebral fractures or distal forearm fractures.

The term "type II osteoporosis" or "age-associated osteoporosis" or "senile osteoporosis" occurs in men or women over the age of 70. The mechanisms of this bone mass loss are thought to be increased PTH secretion resulting from decreased gastrointestinal calcium absorption and decreased osteoblast function. Patients usually present with fractures of the hip or vertebrae, sites that contain cortical and trabecular bone, although fractures of the pelvis, ribs, and tibia can also occur.

The term "osteoporosis" as used herein is defined as a general term for describing any disease process that results in reduction in the mass of bone.

As used herein, the term "in communication" refers to the stimulation lead being adjacent, in close proximity, in contact, or directly next to or directly on the predetermined stimulation site. Thus, one of skill in the art understands that the lead is "in communication" with the predetermined site if the stimulation results in a modulation of neuronal activity.

As used herein, the term "dermatome" refers to the area of skin innervated by a single dorsal root. One of skill in the art realizes that the boundaries of dermatomes are not distinct and in fact overlap because of overlapping innervations by adjacent dorsal roots. Dermatomes are divided into sacral (S), lumbar (L), thoracic (T) and cervical (C). Yet further, as used herein, the term "dermatome" includes all the neuronal tissues located within the region or adjacent to the dermatome area, for example, it may include any peripheral nerve, for example, any cervical nerve root (e.g., C1, C2, C3, C4, C5, C6, C7 and C8) that may innervate the dermatome. For example, the C2/C3 dermatome area may comprise any peripheral nerve (e.g., the occipital nerve (the greater, the lesser, the third and the suboccipital nerve), the great auricular nerve, the transverse cervical nerve, the supraclavicular nerve, spinal accessory nerve, phrenic nerve, dorsal scapular nerve) that arises from the C2 or C3 nerve root.

As used herein the term "modulate" refers to the ability to regulate positively or negatively neuronal activity. Thus, the term modulate can be used to refer to an increase, decrease, masking, altering, overriding or restoring neuronal activity. Modulation of neuronal activity affects fragile bone disorders or conditions of a subject.

As used herein, the term "neuronal" refers to a neuron which is a morphologic and functional unit of the brain, spinal column, and peripheral nerves.

As used herein, the term "nervous system" comprises two components, the central nervous system, which is composed of the brain and the spinal cord, and the peripheral nervous system, which is composed of ganglia and the peripheral nerves that lie outside the brain and the spinal cord. One of skill in the art realizes that the nervous system may be separated anatomically, but functionally they are interconnected and interactive.

As used herein, the term "peripheral nervous system" comprises several parts, for example the autonomic system (parasympathetic and sympathetic), the somatic system and the enteric system.

As used herein, the term "stimulate" or "stimulation" refers to electrical and/or magnetic stimulation that modulates the predetermined sites in the brain.

As used herein, the term "treating" and "treatment" refers to modulating certain areas of the brain so that the subject has an improvement in the disease, for example, beneficial or desired clinical results. For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Differential Activation of the Sympathetic and Parasympathetic Nervous System by C2/C3 Dermatome Electrical Stimulation at Various Frequencies Introduction Bone loss disorders arise from an imbalance in the formation of new healthy bone and the resorption of old bone, skewed toward a net loss of bone tissue. Recently, connections between autonomic nervous system activity and bone growth and loss have been discovered (Kondo et al., 2005; Yirmiya et al., 2006). The inventor applied electrical stimulation to the C2/C3 dermatome at various frequencies and measured changes in sympathetic and parasympathetic autonomic nervous system activity.

Methods

Volunteers were given electrical stimulation at frequencies ranging from 0 to 300 Hz. Adrenaline (epinephrine), noradrenaline (norepinephrine), dopamine and prolactin levels were measured from blood samples after 1 hour of stimulation. Electrocardiograms were recorded and spectral analysis of heart rate variability over 1 hour provided the normalized markers of cardiac sympathetic ($LF_{nu}$) and vagal ($HF_{nu}$) modulation of the sinoatrial node activity and of the sympathovagal balance (LF/HF).

Results

Stimulation at frequencies of 6 Hz and 12 Hz produced a net parasympathetic activation, whereas stimulation at frequencies of 10 Hz and above 18 Hz resulted in greater activation of the sympathetic response.

TABLE 1 shows the levels of adrenaline, noradrenaline, dopamine and prolactin in the bloodstream in response to burst or tonic stimulation of the indicated frequencies between 0 and 40 Hz. As an example in one volunteer stimulation frequencies of 10, 18, 20, and 40 Hz resulted in a robust increase in serum adrenaline levels, whereas stimulation frequencies of 6 and 12 Hz did not. The stimulation frequencies that activate the sympathetic and parasympathetic system might be person specific, but can be determined individually by heart rate variability recordings and measuring adrenaline/noradrenaline blood levels.

TABLE 1

| Patient | 0 Hz | 6 Hz | 10 Hz | 12 Hz | 18 Hz | 20 Hz | 40 Hz |
|---|---|---|---|---|---|---|---|
| Adrenalin Level (nM) after Burst ANS Stimulation at Different Frequencies | | | | | | | |
| MP DDR | 117 | 55 | 62 | 70 | 33 | 70 | 39 |
| 21/5/06 DDR | 43 | 57 | 142 | 31 | 39 | 57 | 317 |
| 29/5/06 | 9 | 23 | 17 | | 32 | 90 | 9 |
| EVDV | 96 | 87 | 58 | 19 | 50 | 18 | 65 |
| Average | 66.3 | 55.5 | 69.8 | 40.0 | 38.5 | 58.8 | 107.5 |
| Adrenalin Level (nM) after Tonic ANS Stimulation at Different Frequencies | | | | | | | |
| MP DDR | 94 | 62 | 62 | 31 | 56 | 55 | 55 |
| 15/5/06 DDR | 55 | 47 | 18 | 80 | 89 | 23 | 19 |
| 26/4/06 EVDV | 39 | 41 | 128 | 80 | 58 | 41 | |
| | 136 | 100 | | | | | |
| Average | 62.7 | 50.0 | 69.3 | 55.5 | 67.7 | 39.7 | 37.0 |
| NorAdrenalin Level (nM) after Burst ANS Stimulation at Different Frequencies | | | | | | | |
| MP | 1132 | 607 | 657 | 686 | 857 | 953 | 654 |
| DDR | 347 | 552 | 429 | 371 | 337 | 368 | |
| EVDV | 405 | 405 | 405 | 330 | 347 | 398 | 438 |
| Average | 628 | 521.3 | 497.0 | 462.3 | 513.7 | 573.0 | 546.0 |
| NorAdrenalin Level (nM) after Tonic ANS Stimulation at Different Frequencies | | | | | | | |
| TM DDR | 357 | 501 | 411 | 342 | 483 | 426 | 538 |
| 15/5/06 DDR | 478 | 480 | 369 | 414 | 352 | 295 | 236 |
| 26/4/06 | 247 | 98 | 152 | 159 | 139 | 117 | |
| MP | 568 | 500 | | | | | |
| Average | 412.5 | 394.8 | 310.7 | 305.0 | 324.7 | 279.3 | 387.0 |
| Dopamine Level (nM) after Burst ANS Stimulation at Different Frequencies | | | | | | | |
| MP DDR | 32 | 65 | 35 | 37 | 70 | 37 | 77 |
| 21/5/06 DDR | 64 | | 53 | | 36 | 53 | |
| 29/5/06 | 122 | 59 | 162 | 34 | 32 | 69 | 36 |
| EVDV | | | 25 | 45 | 58 | 25 | 25 |
| Average | 72.7 | 62.0 | 68.8 | 38.7 | 49.0 | 46.0 | 46.0 |
| Dopamine Level (nM) after Tonic ANS Stimulation at Different Frequencies | | | | | | | |
| MP | 29 | 22 | | | | | |
| TM DDR | 67 | 65 | 135 | 70 | 94 | 120 | 120 |
| 26/4/06 DDR | 56 | 59 | 46 | 116 | 108 | | |
| 15/5/06 | 191 | 128 | 75 | 104 | 31 | 32 | 26 |
| Average | 85.8 | 68.5 | 85.3 | 96.7 | 77.7 | 76.0 | 73.0 |
| Prolactin Level (nM) after Burst ANS Stimulation at Different Frequencies | | | | | | | |
| MP | 148 | 135 | 138 | 122 | 116 | 123 | 147 |
| EVDV DDR | 117 | 79 | 65 | 63 | 58 | 57 | 69 |
| 29/5/06 DDR | 209 | 177 | 205 | 209 | 154 | 151 | 195 |
| 21/5/06 | 132 | 196 | 182 | 231 | 267 | 198 | 195 |
| Average | 151.5 | 146.75 | 147.5 | 156.25 | 148.75 | 132.25 | 151.5 |
| Prolactin Level (nM) after Tonic ANS Stimulation at Different Frequencies | | | | | | | |
| TM DDR | 217 | 284 | 190 | 193 | 198 | 247 | 236 |
| 26/4/06 DDR | 175 | 153 | 150 | 205 | 178 | 276 | |
| 15/5/06 | 186 | 264 | 186 | 231 | 125 | 143 | 160 |
| MP | 153 | 116 | 98 | 106 | 101 | | 113 |
| Average | 182.75 | 204.25 | 156 | 183.75 | 150.5 | 222 | 169.7 |

TABLE 2 shows the HRV Ratio in response to stimulation at frequencies between 0 and 40 Hz. Stimulation frequencies of 0, 10, 18, 20, and 40 Hz resulted in a net increase in the HRV Ratio, whereas stimulation frequencies of 6 and 12 Hz resulted in a net decrease in the HRV Ratio in this person. For other people the frequencies required for activating the parasympathetic and sympathetic system respectively might be different.

TABLE 2

HRV Ratio (LF/HF) after ANS Stimulation at Differnet Frequencies

| Patient | 0 Hz | 6 Hz | 10 Hz | 12 Hz | 18 Hz | 20 Hz | 40 Hz |
|---------|------|------|-------|-------|-------|-------|-------|
| 1 | 1.906 | 0.737 | 1.306 | 0.65 |  | 1.524 | 1.735 |
| 2 | 0.758 | 0.856 | 1.4 |  | 3.37 |  |  |
| Average | 1.332 | 0.7965 | 1.353 | 0.65 | 3.37 | 1.524 | 1.735 |

Discussion

Increased levels of adrenaline in the bloodstream and an increase in LF/HF were both indications of increased sympathetic activity. Conversely, stable adrenaline levels and a decreased LF/HF were indications of increased parasympathetic activity. The inventor found that specific frequencies of autonomic nervous system (ANS) stimulation were capable of eliciting one of these two opposing autonomic responses. Since it has been demonstrated that autonomic balance directly affects the balance between bone growth and bone loss, it is envisaged that specific frequencies of autonomic nervous system stimulation can be applied to promote bone growth and/or inhibit bone loss.

III. Detailed Discussion of the Procedure

The present method acts to stimulate nerve afferents which in turn stimulate the brain and cause/allow the brain to act in the best interest of the host through use of the brain's natural mechanisms. It may come as a surprise to one skilled in the art to learn that stimulation of nervous tissue or at least one of a patient's nerves located in or associated with the C2/C3 dermatome area may be used to treat the maladies disclosed herein. While the normal functions of the nerves associated with the C2/C3 dermatome area would not suggest to one skilled in the art that they could be used to treat, for example, fragile bone disorders, the nerves associated with the C2/C3 dermatome area have qualities which make them suited for the contemplated methods of treatment. For example, an increase in sympathetic tone can mediate deleterious effects on the skeletal system altering bone remodeling and skewing it towards bone resorption thereby increasing the fragility of the skeletal system resulting in fragile bone disorders. Thus, the neurostimulation system can be used to modulate or decrease the sympathetic nervous system by decreasing bone norepinephrine levels or other catecholamines, increasing osteoblast activity, and/or decreasing osteoclast activity.

Figure 4:
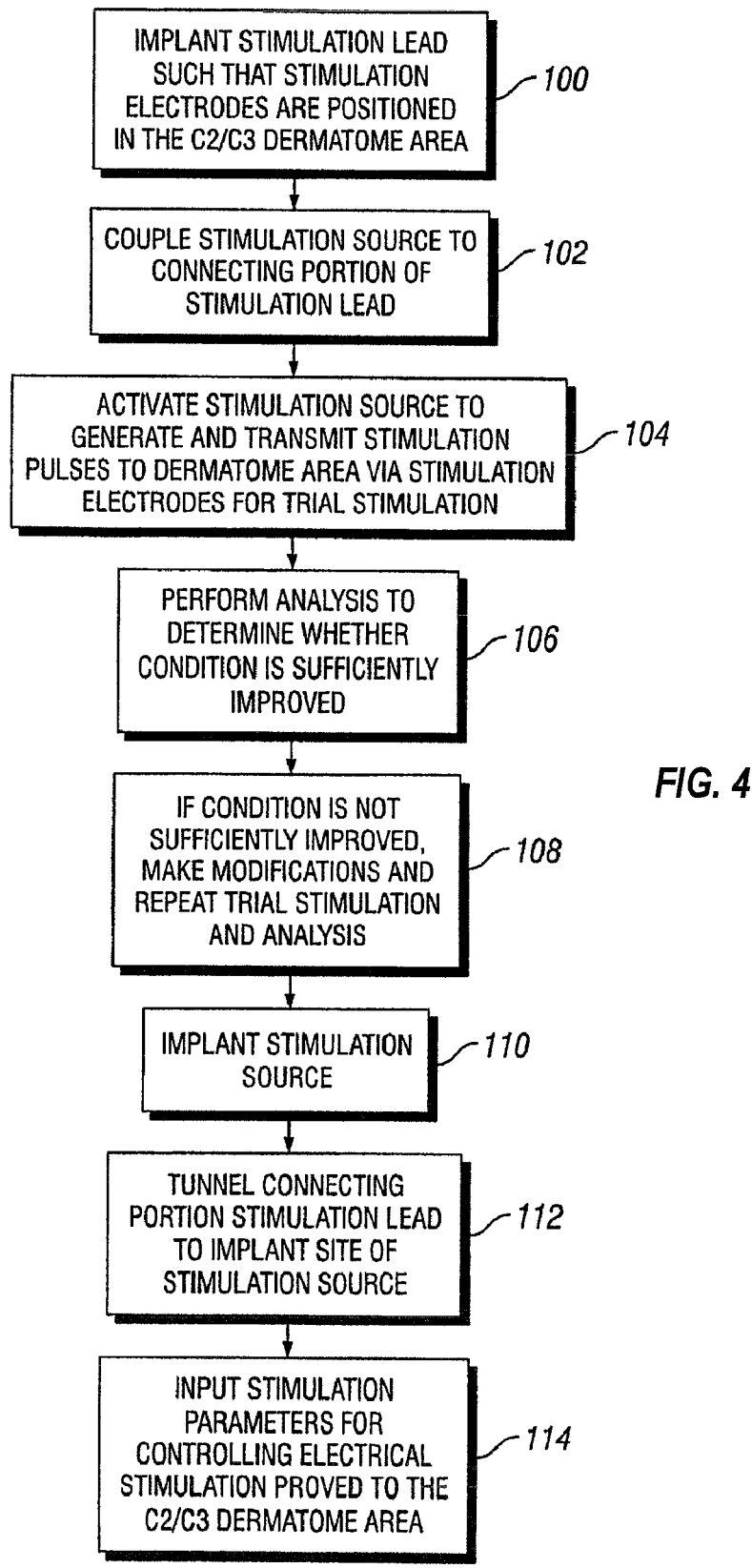
FIG. 4 is a block diagram of steps according to a method for treating fragile bone disorders using a stimulation system.

This section will describe some exemplary details and considerations to be taken into account during the procedure, as further described by FIG. 4. FIGS. 1A-1B illustrate example neurological stimulation systems 10 for stimulating a predetermined area to treat one or more fragile bone conditions. In general terms, stimulation system 10 includes an implantable pulse generating source or stimulation source 12 and one or more implantable electrodes or stimulation leads 14, as illustrated in FIGS. 2A-2I for applying stimulation pulses to the predetermined site, as discussed below.

Implant Stimulation Lead (100)

Figure 3A:
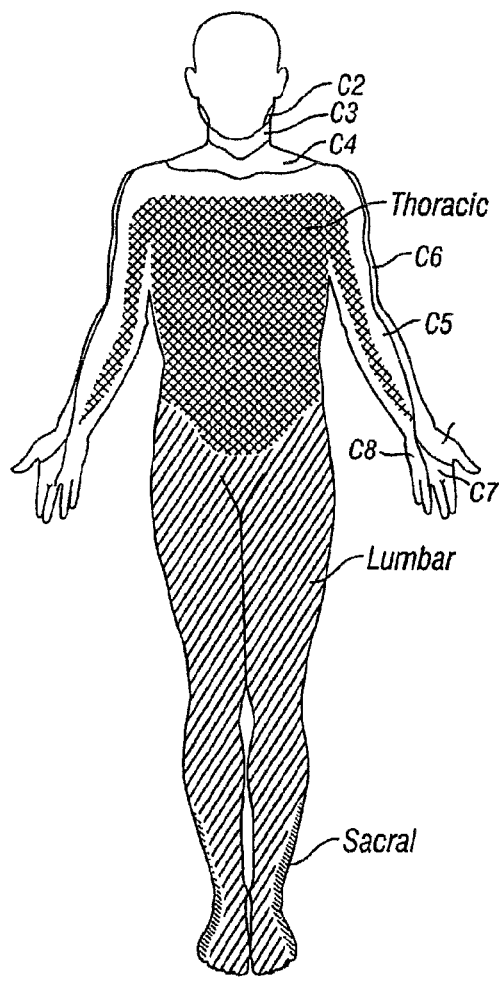
FIGS. 3A-3B illustrate examples of the human dermatome areas, including the cervical dermatomes, including C2 and C3 dermatome.
Figure 3B:
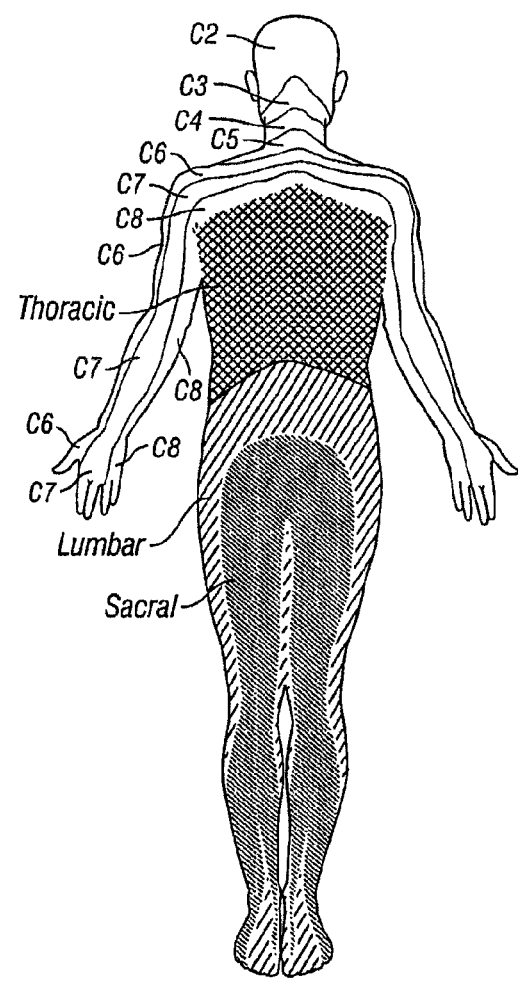

FIGS. 3A-3B illustrate the typical location of the various dermatomes in the human body. The predetermined site may be selected from the group consisting of C2/C3 dermatome area (comprising peripheral nerves such as the occipital nerve (the greater and lesser occipital nerve, lesser occipital nerve, great auricular nerve, third occipital nerve, transverse cervical nerve, supraclavicular nerves, spinal accessory nerve, phrenic nerve, dorsal scapular nerve), cervical nerve roots (e.g., C1, C2, C3, C4, C5, C6, C7 and C8) and/or cranial nerves (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and hypoglossal nerve).

In one exemplary embodiment, the predetermined site is the C2/C3 dermatome area that comprises the cervical nerve roots (C2, C3) and any peripheral nerve that derives or arises from the C2 or C3 cervical nerve roots associated (e.g., the occipital nerve (the greater, the lesser, the third and the suboccipital nerve), the great auricular nerve, the transverse cervical nerve, the supraclavicular nerve, spinal accessory nerve, phrenic nerve, dorsal scapular nerve). In certain embodiments one or more stimulation electrodes 18 are positioned in the C2/C3 dermatome area, subcutaneously, about midline just below the inion or external occipital proturberance.

FIGS. 2A-2I illustrate example stimulation leads 14 that may be used for electrically stimulating the predetermined site to treat one or more fragile bone disorders. As described above, each of the one or more stimulation leads 14 incorporated in stimulation system 10 includes one or more stimulation electrodes 18 adapted to be positioned in communication with the predetermined site and used to deliver to the stimulation pulses received from stimulation source 12. For the purposes described herein, and as those skilled in the art will recognize, when an embedded stimulation system, such as the Bion®, is used, it is positioned similar to positioning the lead 14. Techniques for implanting stimulation leads such as stimulation lead 14 are known to those skilled in the art.

A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions.

A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located.

Although various types of stimulation leads 14 are shown as examples, stimulation system 10 may comprise any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In addition to electrical stimulation, other forms of stimulation can be used, for example magnetic. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Quick pulses of magnetic stimulation can be applied externally or transcranially, for example repetitive transcranially magnetic stimulation (rTMS).

In another embodiment, the stimulation is percutaneous. In "percutaneous" electrical nerve stimulation (PENS), needles are inserted to an appropriate depth around or immediately adjacent to a predetermined stimulation site, and then stimulated.

Couple Stimulation Source to Stimulation Lead
(102)

In certain embodiments, stimulation source 12 is coupled directly to a connecting portion 16 of stimulation lead 14. In certain other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation.

In one embodiment, as shown in FIG. 1, stimulation system 10 comprises implantable pulse generator (IPG) 12, stimulation lead 14, controller 26, and RF transmitter 24. IPG 12 typically comprises a metallic housing that encloses the pulse generating circuitry, control circuitry, communication circuitry, battery, recharging circuitry, etc. of the device. An example commercially available IPG is the EON® IPG available from Advanced Neuromodulation Systems, Inc. IPG 12 also typically comprises a header structure for electrically and mechanically coupling to stimulation lead 14. The electrical pulses generated by IPG 12 are conducted through conductors (not shown) embedded within stimulation lead 14 and delivered to tissue of the patient using electrodes 18 at distal end 20 of stimulation lead 14. Furthermore, IPG 12 may be adapted to communicate with external devices, such as controller 26, after implantation within a patient. For example, controller 26 may utilize RF transmitter 22 to conduct wireless communications 24 with IPG 12 after IPG 12 is implanted within a patient.

In one embodiment, the stimulation source transcutaneously stimulates target neural tissue. In "transcutaneous" electrical nerve stimulation (TENS), a stimulation source and one or more patch electrodes are disposed external to the patient. The stimulation source may be worn in an appropriate fanny pack or belt. The patch electrode is typically applied on the skin immediately above the appropriate neural tissue. The stimulation source delivers electrical stimulation to the patch electrode thereby stimulating the adjacent neural tissue.

Generate and Transmit Trial Stimulation Pulses
(104)

Stimulation source 12 controls the stimulation pulses transmitted to one or more stimulation electrodes 18 located on a stimulating portion 20 of stimulation lead 14, positioned in communication with a predetermined site to stimulate peripheral nerves, according to suitable stimulation parameters (e.g., duration, amplitude or intensity, frequency, pulse width, etc.). At step 104, stimulation source 12 is activated to generate and transmit stimulation pulses via one or more stimulation electrodes 18. A doctor, the patient, or another user of stimulation source 12 may directly or indirectly input stimulation parameters for controlling the nature of the stimulation provided.

It is envisaged that the patient will require intermittent assessment with regard to patterns of stimulation. Different electrodes on the lead can be selected by suitable programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

In some embodiments, a doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the stimulation parameters of stimulation pulses transmitted through stimulation lead 14 to the predetermined site. Thus, the external controller 26 can be for example, a handheld programmer, to provide a means for programming the IPG. Also, external controller 26 and transmitter 22 can be integrated in a single device.

Assess Stimulation Efficacy (106)

At step 106, a doctor may conduct tests or analyses for example to determine bone mass, to determine norepinephrine levels, and/or to determine osteoblast/osteoclast activity. Fragile bone disorders can be monitored by measuring bone mineral density (BMD) using standard techniques, for example dual-energy x-ray absorptiometry (DEXA), and quantitative computed tomography (QCT). Peripheral bone density testing can also be used.

Modify Protocol and Repeat Trial Stimulations (108)

If the one or more fragile bone disorders and/or conditions are not sufficiently improved, one or more stimulation parameters may be adjusted, stimulation lead 14 may be moved incrementally or even re-implanted, or both of these modifications may be made at step 108 and the trial stimulation and analysis repeated until the one or more fragile bone disorders and/or conditions are sufficiently improved. Once the stimulation parameters have been properly set and stimulation lead 14 has been properly positioned such that the one or more conditions are sufficiently improved, intra-implantation trial stimulation is complete.

In some embodiments, it is considered that several cycles of intra-implantation trials may be required. In preferred embodiments, a comparison of the treatment efficacy between multiple cycles of intra-implantation trial stimulation will be used to determine the optimal location and stimulation protocol. In further embodiments, steps 104 through 108 represent a repetitive cycle that ends when an optimal location and protocol have been selected. In some embodiments, once the stimulation lead 14 has been properly positioned such that bone resorption is reduced and/or bone growth is increased, intra-implantation trial stimulation may be considered complete. In other embodiments, the intra-implantation trial stimulation is not performed, and the method proceeds from process 102 to 110. It is contemplated that stimulation parameters may be modified to maximize the effectiveness of the therapy both prior to and subsequent to the end of the intra-implantation trial stimulations.

Parameters relating to fragile bone disorders can be measured to determine improvement or efficacy of the treatment. Such the parameters can include increase in bone density, increase in bone strength, induction of healthy bone growth, decrease in bone fractures and/or breaks, modulation of calcium levels, and modulation of mineral accumulation in the skeleton, decrease in bone norepinephrine levels, decrease in osteoclast activity, increase osteoblast in levels, increase in T-scores of at least −1 or above, increase in Z-scores. The improvement is any observable or measurable improvement. Thus, one of skill in the art realizes that a treatment may improve the patient condition, but may not be a complete cure of the disease.

Implant Stimulation Source (110)

Once stimulation lead 14 has been properly implanted and secured, and any trial stimulation completed, if necessary, stimulation source 12 is implanted at step 110. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the upper chest or buttocks.

Tunnel Connection Between Stimulation Lead and Stimulation Source (112)

Where stimulation lead 14 includes connecting portion 16, connecting portion 16 may be tunneled, at least in part, subcutaneously to the implant site of stimulation source 12 at step 112.

Input Stimulation Parameters (114)

At step 114, a doctor, the patient, or another user of stimulation source 12 may directly or indirectly input stimulation parameters for controlling the nature of the electrical stimulation provided to the C2/C3 dermatome area, if not already set during any intra-implantation trial stimulation period. Where appropriate, post-implantation trial stimulation may be conducted, over one or more weeks or months for example, and any necessary modifications made accordingly.

Stimulation parameters can include pulse width of about 1 to about 1000 microseconds, more preferable, about 50 to about 500 microseconds; frequency of about 3 to about 40 Hz, more preferably, about 3 to about 20 Hz, more preferably, 6 to about 12 Hz; and amplitude of about 1 to about 100 mA, more preferably about 1 to about 30 mA. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

In another embodiment, a neuromodulation device can be implemented to apply burst stimulation parameters. Examples of burst stimulation are found in U.S. Published Application No. US20060095088, and incorporated herein by reference in its entirety. The burst stimulation may generate bursts of a plurality of electrical pulses with an inter-burst frequency in the range of about 1 Hz to about 100 Hz, more particular, in the range of about 1 Hz to about 50 Hz. The inter-burst interval has a duration in the range of about 1 milliseconds to about 5 seconds, more preferably, about 10 milliseconds to about 300 milliseconds. The inter-burst interval need not be constant and can be varied in a programmable manner or varied pseudo-randomly by the pulse generator (e.g., random or irregular harmonics).

The patient can be in control of the stimulation parameters and/or programs to maintain effectiveness of the stimulation system. For example, the patient can change the programs on a periodic basis, for example weekly to maintain effectiveness. Other patients may increase the stimulation during the day and decrease the stimulation parameters during the evening or vice versa.

Thus, it may be desirable for the patient to control the therapy to optimize the operating parameters to achieve the desired result of decreased bone loss or management of bone loss or treatment of fragile bone disorders or management of bone growth. For example, the patient can alter the pulse frequency, pulse amplitude and pulse width using a hand held radio frequency device that communicates with the IPG. Once the operating parameters have been altered by the patient, the parameters can be stored in a memory device to be retrieved by either the patient or the clinician. Yet further, particular parameter settings and changes therein may be correlated with particular times and days to form a patient therapy profile that can be stored in a memory device.

Following post-implantation, the efficacy of the system can be determined by utilizing any of the well known and described methods to assess various or evaluate improvements of symptoms associated with a fragile bone disease and/or disorder. Exemplary methods are described above under step 106 and incorporated herein by reference.

Although example steps are illustrated and described, the present application contemplates two or more steps taking place substantially simultaneously or in a different order. In addition, the present application contemplates using methods with additional steps, fewer steps, or different steps, so long as the steps remain appropriate for implanting stimulation system 10 into a person for stimulation of the a predetermined site, such as C2/C3 dermatome area to treat one or more fragile bone disorders or conditions.

IV. Types of Fragile Bone Conditions, Disorders, or Diseases

Osteoporosis is common in the elderly of both sexes but is more pronounced in postmenopausal women. Osteoporosis may occur as a primary disorder or as a secondary complication of several diseases. It is proposed that genetic factors determine the size of the bone mass achieved in young adulthood. With aging, the increased osteoclastic function and the slowing of osteoblastic activity induced by endocrine influences, particularly decreased estrogen levels, result in a net negative balance in the continued turnover of bone. Osteoporosis causes bone pain owing to microfractures; results in loss in height and stability of the vertebral column; and predisposes to fractures of femoral necks, wrists, and vertebrae. The condition remains asymptomatic until skeletal fragility is well advanced.

Paget's disease is currently considered to be a slow paramyxoviral infection of osteoblasts and then osteoclasts. The condition is divided into an initial osteolytic stage, followed by a mixed osteolytic-osteoblastic stage, evolving ultimately into burn-out quiescent osteosclerotic stage. Because new bone formation in active disease is disordered and poorly mineralized, it is soft and porous, lacks structural stability, and is vulnerable to fracture or deformation under stress. Patients may demonstrate fractures, nerve compression, osteoarthritis, and skeletal deformities.

Osteogenesis imperfecta or brittle bones refers to a group of closely related genetic disorders caused by qualitative or quantitative abnormal synthesis of type I collagen, constituting about 90% of the matrix of bone. Syndromes range from one variant (type II) that is uniformly fatal in the perinatal period (from multiple bone fractures) to other variants marked by increased predisposition to fracture but compatible with survival. Morphologically the basic change in all is osteopenia or too little bone, with marked thinning of the cortices and rarefication of the trabeculae.

Osteopetrosis refers to a group of rare hereditary diseases characterized by overgrowth and sclerosis of bone, with marked thickening of the cortex and narrowing or filling of the medullary cavity impairing hematopoiesis. Despite too much bone, it is brittle and fractures easily. The autosomal recessive form is evident from birth, with anemia, neutropenia, infections and eventual death. The autosomal dominant form is benign but predisposes to fractures. Common to all forms is a hereditary defect in osteoclast function resulting in reduced bone resorption and enhanced net bone overgrowth.

Fragile bone disorders can be diagnosed and/or monitored by measuring bone mineral density (BMD) using standard techniques, for example dual-energy x-ray absorptiometry (DEXA), and quantitative computed tomography (QCT). Peripheral bone density testing can also be used. BMD measurement is given as a T-score and a Z-score. The T score compares the patients's bone density with the average bone density of 25- to 30-year-olds of the same sex. This age group is used because bone density is at its highest at this age. A T-score of at least −1 to 0 or greater is considered normal. A T-score between −1 and −2.5 indicates some bone loss (osteopenia) and a risk of osteoporosis. A T-score of less than −2.5 is diagnostic of osteoporosis. The Z score compares a patient's bone density with that of people of the same age, sex, weight, and ethnic or racial origin. The Z-score can be used to classify the type of osteoporosis. A score of at about −1.5 indicates primary osteoporosis, which is age related. A score of less than −1.5 can indicate secondary osteoporosis, which is associated with calcitonin imbalance, malabsorption conditions (e.g., celiac disease, cystic fibrosis).

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of treating a fragile bone disorder in a patient comprising:
   surgically implanting a stimulation lead subcutaneously with one or more electrodes in contact with a C2/C3 dermatome area in the patient identified as having a fragile bone disorder;
   coupling the stimulation lead to a pulse generator;
   programming the pulse generator to generate stimulating pulses at a frequency that is effective in modifying sympathetic or parasympathetic response in the subject;
   operating the pulse generator according to the programming to generate stimulation pulses for delivery to the C2/C3 dermatome area using one or more electrodes of the stimulation lead to treat the fragile bone disorder; and
   examining the patient to determine whether the stimulation pulses are effective in affecting bone density in the patient.

2. The method of claim 1, wherein the efficacy of the treatment increases according to the amplitude of the stimulation pulses.

3. The method of claim 1, wherein the fragile bone disorder is osteoporosis.

4. The method of claim 1, wherein the stimulation lead is a percutaneous lead.

5. The method of claim 1, wherein the stimulation lead is a laminotomy, paddle, or surgical lead.

6. The method of claim 1, wherein the stimulation lead and the pulse generator are contained in one unit.

7. The method of claim 1, wherein the stimulation decreases bone norepinephrine levels.

8. The method of claim 1, wherein the stimulation decreases osteoclast activity.

9. The method of claim 1, wherein the stimulation increases osteoblast activity.

* * * * *